United States Patent
Brechbiel et al.

(12)
(10) Patent No.: US 6,696,551 B1
(45) Date of Patent: Feb. 24, 2004

(54) $^{225}$AC-HEHA AND RELATED COMPOUNDS, METHODS OF SYNTHESIS AND METHODS OF USE

(75) Inventors: Martin W. Brechbiel, Annandale, VA (US); Kim Deal, Springfield, VA (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 09/937,030

(22) PCT Filed: Mar. 23, 2000

(86) PCT No.: PCT/US00/07643

§ 371 (c)(1),
(2), (4) Date: Dec. 20, 2001

(87) PCT Pub. No.: WO00/59896

PCT Pub. Date: Oct. 12, 2000

Related U.S. Application Data

(60) Provisional application No. 60/125,764, filed on Mar. 23, 1999.

(51) Int. Cl.$^7$ .................................................. C07F 5/00
(52) U.S. Cl. ........................... 534/10; 534/7; 424/1.11; 424/1.65; 424/9.1
(58) Field of Search ............................... 424/1.11, 1.65, 424/9.1, 1.49, 1.69; 534/7, 10; 540/450

(56) References Cited

U.S. PATENT DOCUMENTS

| | | |
|---|---|---|
| 5,246,691 A | 9/1993 | Geerlings et al. |
| 5,435,990 A | 7/1995 | Cheng et al. |
| 5,808,003 A | 9/1998 | Subramanian et al. |

FOREIGN PATENT DOCUMENTS

| | | |
|---|---|---|
| JP | 03 197468 | 8/1991 |

OTHER PUBLICATIONS

Beyer et al., *Nuclear Medicine & Biology* 24:367–372 (1997).

Beyer et al., *Isotopenpraxis* 26:111–114 (1990).

Deal et al., *J. Med. Chem.* 42:2988–2992 (1999).

*Primary Examiner*—Dameron L. Jones
(74) *Attorney, Agent, or Firm*—Leydig, Voit & Mayer Ltd.

(57) ABSTRACT

The present invention provides an α-particle-emitting radio-isotope chelation complex comprising $^{225}$Actinium ($^{225}$Ac) and 1,4,7,10,13,16-hexaazacyclohexadecane-N,N',N'',N''',N'''',N'''''-hexaacetic acid (HEHA) ($^{225}$Ac-HEHA). Also provided is a bifunctional HEHA, and a bifunctional $^{225}$Ac-HEHA. The bifunctional HEHA and the bifunctional $^{225}$Ac-HEHA can be conjugated to a targeting agent. In view of the above, the present invention provides a method of making HEHA and methods of making a bifunctional HEHA, including a conjugate thereof. Also provided are a method of treating disease, a method of treating cancer, a method of decontaminating a sample from $^{225}$Ac, a method of decontaminating a person who has been externally contaminated with $^{225}$Ac, and a method of detoxifying a person who has internalized $^{225}$Ac.

14 Claims, No Drawings

225Ac-HEHA AND RELATED COMPOUNDS, METHODS OF SYNTHESIS AND METHODS OF USE

CROSS-REFERENCE TO RELATED PATENT APPLICATIONS

This patent application is the U.S. National Phase of PCT/US00/07643 filed on Mar. 23, 2000, which claims priority to U.S. provisional patent application No. 60/125,764 filed on Mar. 23, 1999.

TECHNICAL FIELD OF THE INVENTION

The present invention relates to a chelation complex comprising $^{225}$Actinium ($^{225}$Ac) and 1,4,7,10,13,16-hexaazacyclooctadecane-N,N',N'',N''',N'''',N'''''-hexaacetic acid (HEHA) ($^{225}$Ac-HEHA), bifunctional HEHA, bifunctional HEHA-targeting agent, bifunctional $^{225}$Ac-HEHA, bifunctional $^{225}$Ac-HEHA-targeting agent, and methods of synthesis and use, such as in the context of radioimmunotherapy, decontamination and detoxification.

BACKGROUND OF THE INVENTION

In the field of radioimmunotherapy, the radioisotope chosen is determined, at least in part, by the type of disease to be treated. The reason for this is that the type of particles emitted by a given radioisotope are directly related to tissue penetration and the ability of the isotope to kill cells (Boll et al., Radiochim. Acta 79: 87–91 (1997)). β-emitters, like $^{90}$Y and $^{131}$I, which have a tissue range of several millimeters, have been used successfully to treat solid tumors (Boll et al. (1997), supra). However, a tissue range of several millimeters is not optimal for the treatment of single cells, small clusters of cells, micrometastatic disease, leukemias and lymphomas (Jurcic et al., In: *Cancer Chemotherapy and Biological Response Modifiers Annual* 17, Pinedo et al., eds., New York: Elsevier B. V. (1998), pp. 195–216; Falini et al., *Cancer Surveys* 30: 295–309 (1998)). α-emitters, on the other hand, combine high cytotoxicity with a short tissue range, i.e., less than about 150 μ (Boll et al. (1997), supra). Alpha radiation can kill a cell with only one hit to the nucleus and will kill substantially any cell with 10 hits or less. Consequently, considerable effort has been expended in the development of the α-emitters $^{212}$Bi ($t_{1/2}$=60 min) (Ruegg et al., *Cancer Res.* 50: 4221–4226 (1990)), $^{213}$Bi ($t_{1/2}$=45 min) (Geerlings et al., *Nucl. Med. Comm.* 14: 121–125 (1993)), and $^{211}$At ($t_{1/2}$—7.2 hr) (Lambrecht et al., *Radiochim. Acta* 36: 443–440 (1985)). However, $^{212}$Bi, $^{213}$Bi and $^{211}$At suffer from disadvantages. The short half-life of $^{212}$Bi and $^{213}$Bi limit their application. The limited available of $^{211}$At, due to half-life and production constraints, limits its utility. Consequently, $^{225}$Ac, which is highly cytotoxic, has been proposed as an alternative α-emitter to $^{212}$Bi, $^{213}$Bi and $^{211}$At for use in radioimmunotherapy.

$^{225}$Ac decays through a chain of four α emissions and two β emissions to the stable isotope $^{209}$Bi, thereby releasing a large amount of energy (28 MeV) (Davis et al., *Nucl. Med. Biol.*, accepted; Alleluia et al., In: *Gmelin Handbook of Inorganic Chemistry*, 8$^{th}$ ed., Kugler et al., eds., New York: Springer-Verlag (1981), pp. 181–193). Unfortunately, most of the $^{221}$Ac administered in a dose is deposited in the liver and bone (Beyer et al., *Isotopenpraxis* 26: 111–114 (1990)). Thus, numerous attempts have been made to reduce the toxicity of $^{225}$Ac through chelation with, for example, citrate (Beyer et al. (1990), supra), EDTMP (ethylenediaminetetramethylenephosphonic acid; Beyer et al., *Nucl. Med. Bio.* 24:367–372 (1997)), EDTA (ethylenediaminetetraacetic acid; Alleluia et al. (1981), supra) and CHXA"-DTPA (N[(R)-2-amino-3-(4-nitrophenyl)propyl]-trans-(S,S)-cyclohexane-1,2-diamine-N,N,N',N'',N''-pentaacetic acid; Davis et al., supra). While these chelates reduce the liver dose somewhat, CHXA"-DTPA, which is the best $^{225}$Ac chelate to date, still has a maximum tolerated dose (MTD) of approximately 100 kBq in mice and higher doses of $^{225}$Ac-CHX-DTPA have resulted in 100% mouse mortality within eight days (Davis et al., supra).

Thus, while $^{225}$Ac is potentially useful in radioimmunotherapy, a suitable chelate is needed. Until now, a suitable chelate with sufficient in vivo stability had yet to be discovered. Certain bifunctional large cyclic chelate ligands are described in JP3-197468. However, there is no teaching or suggestion in JP3-197468 that the disclosed ligands would be useful to chelate $^{225}$Ac. Accordingly, it is an object of the present invention to provide chelated $^{225}$Ac. It is another object of the present invention to provide methods of synthesizing the chelate and related compounds. It is yet another object of the present invention to provide methods of using the chelate and related compounds. These and other objects, as well as additional advantages and inventive features, will become apparent from the detailed description provided herein.

BRIEF SUMMARY OF THE INVENTION

The present invention provides an α-particle-emitting radioisotope chelation complex comprising $^{225}$Actinium ($^{225}$Ac) and 1,4,7,10,13,16-hexaazacyclooctadecane-N,N',N'',N''',N'''',N'''''-hexaacetic acid (HEHA) ($^{225}$Ac-HEHA). Also provided is a bifunctional HEHA which can chelate a radiosotope, in particular $^{225}$Ac, and can be attached to a targeting agent, such as a bifunctional HEHA having one of the following formulae:

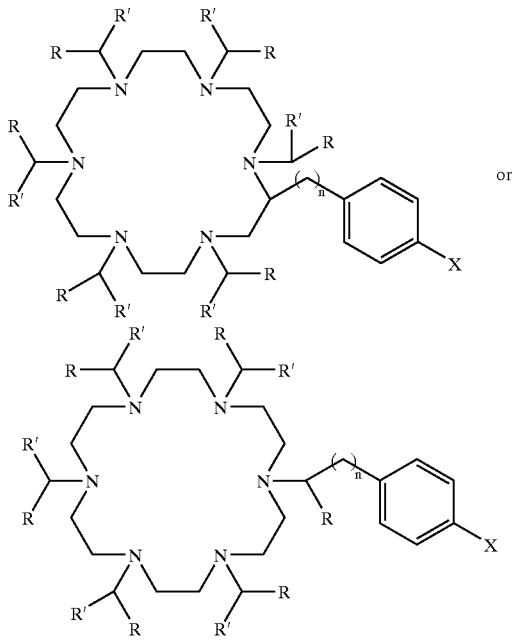

wherein R is $CO_2H$, $CONHR'$, $P(O)R'OH$ or $P(O)(OR')CH$, R' is H, a $C_1$–$C_8$ alkyl, phenyl or benzyl, wherein said phenyl or benzyl is unsubstituted or substituted, n is 1–6, X is $NO_2$, $NH_2$, NCS, $NHC(O)CH_2Z$ (in which Z is Cl, Br or I), or

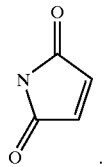

Other bifunctional HEHAs are set forth herein. A compound comprising the bifunctional HEHA conjugated to a targeting agent is also provided. Accordingly, further provided is a bifunctional $^{225}$Ac-HEHA complex comprising $^{225}$Ac complexed with the bifunctional HEHA described above as well as a compound comprising the bifunctional $^{225}$Ac HEHA complex conjugated to a targeting agent.

In view of the above, the present invention further provides a method of making HEHA. The method comprises preparing the free base of 1,4,7,10,13,16-hexaazacyclooctodecane under anhydrous conditions, azeotropically removing trace water with benzene, N-alkylating the macrocycle to produce the hexaester, saponifying the hexaester, and purifying HEHA. Preferably, the hexaester is produced by reacting the free base with $Na_2CO_3$ and tert-butyl bromoacetate in anhydrous $CH_3CN$.

Still further provided is a method of making a bifunctional HEHA. The method comprises the preparation of a tert-butyloxycarbonyl protected iminodiacetic acid that is condensed with an amino acid ester. The resulting diester is then saponified with base, and after acidification, converted to a disuccinimidyl ester. This active diester is then reacted with an N-2-aminoethyl amide of para-nitrophenylalanine that introduces the latent bifunctionality aspect that will be unmasked. The protecting group is removed by treatment with acid, and the amide carbonyl functional groups are reduced via diborane. The resulting macrocyclic polyamine is isolated as the protonated salt. The free base is generated and then the free amines are alkylated to introduce protected R groups. The protected R groups are then deprotected. The nitro group is then hydrogenated to the aniline, which is then converted to an isothiocyanate, a haloacetamide or a maleimide for conjugation to a targeting agent. The method can further comprise the conjugation of a bifunctional HEHA to a targeting agent. Alternatively, the method comprises the preparation of a cyclic hexapeptide that comprises para-nitrophenylalanine or ε-protected lysine and the subsequent reduction of amide carbonyl functional groups. The resulting macrocyclic polyamine is isolated as the protonated salt. The free base is then generated and the free amines are alkylated to introduce protected R groups, which are subsequently deprotected. The nitro group is hydrogenated to the aniline and the aniline is converted to an isothiocyanate, a haloacetamide or a maleimide, any one of which can then be conjugated to a targeting agent.

In another embodiment, a method of treating disease is provided. The method comprises administering to a patient having disease a disease-treatment effective amount of a $^{225}$Ac-HEHA targeting agent as described above in which the targeting agent is specific for diseased cells.

In yet another embodiment, a method of treating cancer is also provided. The method comprises administering to a patient having cancer a cancer-treatment effective amount of a $^{225}$Ac-HEHA-targeting agent as described above in which the targeting agent is specific for the cancer to be treated. In a related embodiment, a method of treating a solid tumor is provided. The method comprises intratumorally administering to a patient having a tumor a tumor-treatment effective amount of $^{225}$Ac-HEHA or $^{225}$Ac-HEHA-targeting agent in which the targeting agent is specific for the tumor. Optionally, the method further comprises simultaneously or sequentially peritumorally administering to the patient HEHA in an amount effective to chelate any radioactive decay products from the compound.

In still yet another embodiment, a method of decontaminating a sample from $^{225}$Ac is provided. The method comprises contacting the sample with a decontaminating-effective amount of HEHA.

A further embodiment is a method of decontaminating a person who has been externally contaminated with $^{225}$Ac. The method comprises contacting the person with a decontaminating-effective amount of HEHA. Similarly, a method of detoxifying a person who has internalized $^{225}$Ac is provided. The method comprises administering to the person a detoxifying-effective amount of HEHA.

DETAILED DESCRIPTION OF THE INVENTION

The present invention is predicated on the surprising and unexpected discovery that HEHA chelates $^{225}$Ac in such a manner as to provide sufficient in vivo stability to enable its use in the context of radioimmunotherapy and other contexts. Accordingly, in one embodiment, the present invention provides an α-particle-emitting radioisotope chelation complex comprising $^{225}$Ac and HEHA. $^{225}$Ac-HEHA is highly desirable because it comprises $^{225}$Ac, which is a metal radioisotope with excellent cytotoxicity that forms a suitable complex with HEHA having a half-life (i.e., approximately 10.5 days, wherein from about 30 min to about 3 wks is preferred and from about 30 min to about 11 days is more preferred) and an emission quality that are characteristic of radiopharmaceuticals and a toxic radioactive decay chain that results in nonradioactive material as a final product.

In view of the above, the present invention further provides a bifunctional HEHA which can chelate a radiosotope, which is preferably $^{225}$Ac, and can attach to a targeting agent, such as described herein. HEHA can be rendered bifunctional in any suitable manner in accordance with methods known in the art (see, e.g., Wang, *Chemistry of Protein Conjugation and Crosslinking*, CRC Press, Boca Raton, Fla. (1991); Lundblad, *Chemical Reagents for Protein Modification*, CRC Press, Boca Raton, Fla. (1991)). Preferred bifunctional HEHAs include those of the following formulae:

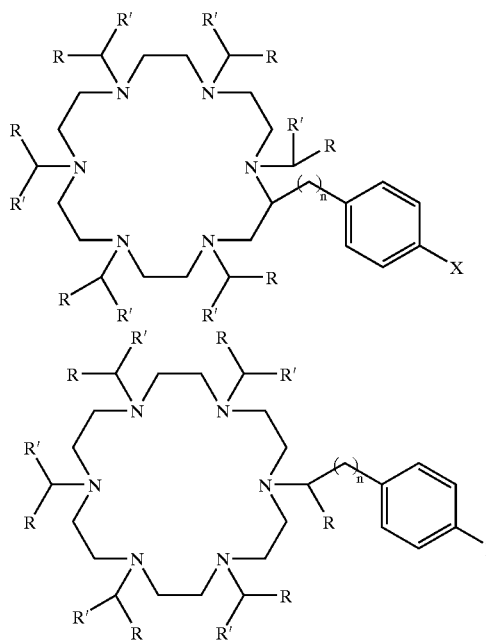

or

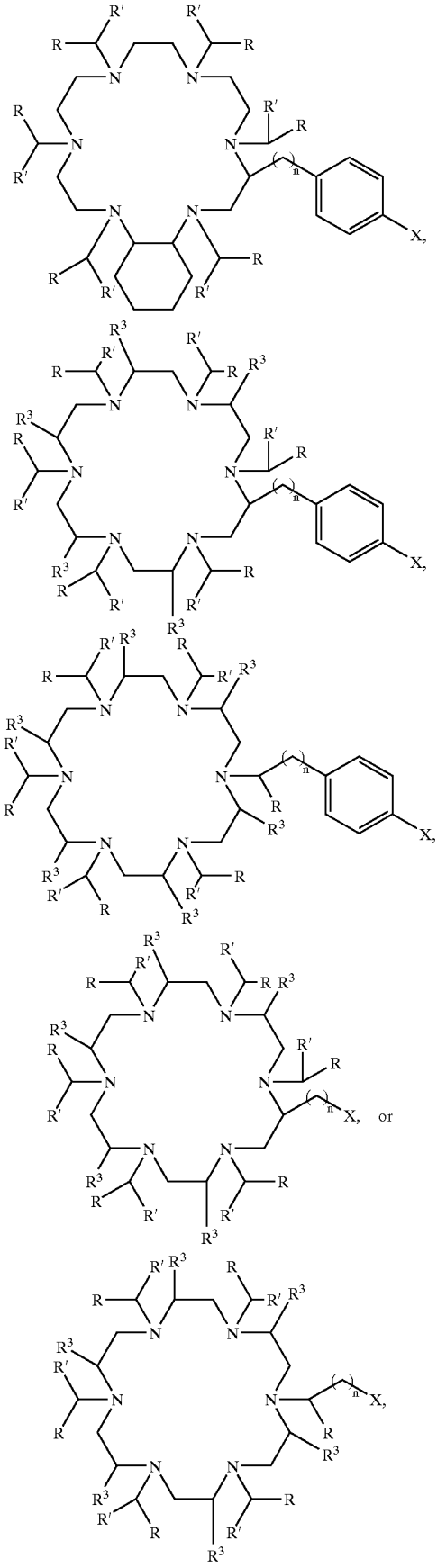

wherein R is selected from the group consisting of $CO_2H$, $CONHR'$, $P(O)R'OH$ and $P(O)(OR')OH$, R' is selected from the group consisting of H, a $C_1$–$C_8$ alkyl, phenyl and benzyl, wherein phenyl and benzyl are substituted or unsubstituted, n is 1–6 and, X is selected from the group consisting of $NO_2$, $NH_2$, NCS, $NHC(O)CH_2Z$ (in which Z is selected from the group consisting of Cl, Br and I), and

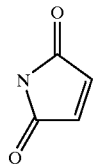

Preferably, R is $CO_2H$ and R' is H or $CH_3$. When R' is phenyl or benzyl, phenyl or benzyl can be substituted with one or more substituents selected from the group consisting of a $C_1$–$C_6$ alkyl, a halogen, a $C_1$–C6 alkoxy, a $C_1$–$C_6$ hydroxyl, and a $C_1$–$C_6$ poly-hydroxyl.

Other bifunctional HEHAs include those of formulae:

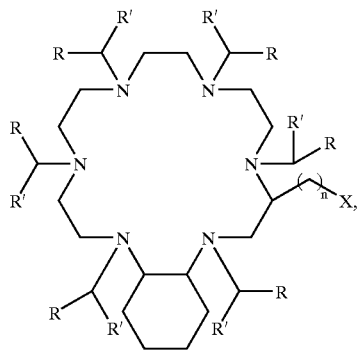

wherein R, R', n and x are as defined above and R³ is selected from the group consisting of H, a $C_1$–$C_6$ alkyl, and benzyl.

Further in view of the above, the present invention provides a compound comprising the above-described bifunctional HEHA conjugated to a targeting agent. By "targeting agent" is meant any means that enables specific interaction with a target. The targeting agent can bind to a defined population of cells, for example, through a receptor, a substrate, an antigenic determinant or another binding site on the target cell population.

Cell-surface molecules that are cancer specific antigens (or disease-specific antigens) and can serve as targets are known in the art.

Examples of cancer-specific, cell-surface molecules include placental alkaline phosphatase (testicular and ovarian cancer), pan carcinoma (small cell lung cancer), polymorphic epithelial mucin (ovarian cancer), prostate-specific membrane antigen, α-fetoprotein, β-lymphocyte surface antigen (B-cell lymphoma), truncated EGFR (gliomas), idiotypes (B-cell lymphoma), gp95/gp97 (melanoma), N-CAM (small cell lung carcinoma), cluster w4 (small cell lung carcinoma), cluster 5A (small cell carcinoma), cluster 6 (small cell lung carcinoma), PLAP (seminomas, ovarian cancer, and non-small cell lung cancer), CA-125 (lung and ovarian cancers), ESA (carcinoma), CD19, 22 or 37 (B-cell lymphoma), 250 kD proteoglycan (melanoma), P55 (breast cancer), TCR-IgH fusion (childhood T-cell leukemia), blood group A antigen in B or O type individual (gastric and colon tumors), and the like.

Examples of cancer-specific, cell-surface receptors include erbB-2, erbB-3, erbB-4, IL-2 (lymphoma and leukemia), IL-4 (lymphoma and leukemia), IL-6 (lymphoma and leukemia), MSH (melanoma), transferrin (gliomas), tumor vasculature integrins, and the like. Preferred cancer-specific, cell-surface receptors include erbB-2 and tumor vasculature integrins, such as CD11a, CD11b, CD11c, CD18, CD29, CD51, CD61, CD66d, CD66e, CD106, and CDw145.

The erbB-2 receptor has been found in breast, ovarian, gastric, salivary gland and adeno-carcinomas and in non-small cell carcinomas of the lung. Over-expression of the erbB-2 receptor on such cancers has been found to correlate with poor prognosis. In vitro studies strongly suggest that over-expression of erbB-2 may play an important role in tumor progression.

An example of a single-chain antibody scAb is that which binds c-erbB-2 (WO 93/16185). See, also, WO 93/21232 and H. Zola, *Monoclonal Antibodies*, BIOS Scientific Publishers, Oxfordshire, England (November 1994) antibody sequences that can be used to construct scAbs.

There are a number of antibodies to cancer-specific, cell-surface molecules and receptors that are known. C46 Ab (Amersham) and 85A12 Ab (Unipath) to carcino-embryonic antigen, H17E2 Ab (ICRF) to placental alkaline phosphatase, NR-LU-10 Ab (NeoRx Corp.) to pan carcinoma, HMFC1 Ab (ICRF) to polymorphic epithelial mucin, W14 Ab to B-human chorionic gonadotropin, RFB4 Ab (Royal Free Hospital) to B-lymphocyte surface antigen, A33 Ab (Genex) to human colon carcinoma, TA-99 Ab (Genex) to human melanoma, antibodies to c-erbB2 (JP 7309780, JP 8176200 and JP 7059588), and the like. ScAbs can be developed, based on such antibodies, using techniques known in the art (see, for example, Bind et al., Science 242: 423–426 (1988), and Whitlow et al., Methods 2(2): 97–105 (1991)).

Examples of binding domains include the EGF domain of α-heregulin, α-integrin domain, tumor vasculature peptide motifs. Alpha-heregulin is a ligand with affinity for breast cancer cells expressing the human epidermal growth factor receptors erbB-2, erbB-3 and erbB-4. Heregulin interacts indirectly with erbB-2 via heterodimerization with erbB-3 or erbB-4.

In general, there are a number of databases for ligands, binding domains and cell-surface molecules.

Examples of a targeting agent include an "immunological agent," which is used herein to refer to an antibody, such as a polyclonal antibody or a monoclonal antibody, an immunologically reactive fragment of an antibody, an engineered immunoprotein and the like, a protein (target is receptor, as substrate, or regulatory site on DNA or RNA), a peptide (target is receptor), a nucleic acid (target is complementary nucleic acid), a steroid (target is steroid receptor), and the like. Preferred targeting agents include an antibody or an iummunologically reactive fragment thereof, a peptide, e.g., bombesin, gastrin-releasing peptide, RGD peptide, substance P, neuromedin-B, neuromedin-C, somatostatin, octreotide analogues, and metenkephalin, and a hormone, e.g., estradiol, neurotensin, melanocyte stimulating hormone, follicle analogues stimulating hormone, leutenizing hormone, and human growth hormone. Other suitable targeting agents include serum proteins, fibrinolytic enzymes, and biological response modifiers, such as interleukin, interferon, erythropoietin, and colony-stimulating factor. Analogs of targeting agents that retain the ability to bind to a defined target also can be used. In addition, synthetic targeting agents can be designed, such as to fit a particular epitope. The targeting agent can include any linking group that can be used to join a targeting agent to, in the context of the present invention, a chelate. It will be evident to one skilled in the art that a variety of linking groups, including bifunctional reagents, can be used.

Accordingly, the present invention further provides a bifunctional $^{225}$Ac-HEHA comprising $^{225}$Ac complexed with a bifunctional HEHA as described above. Also, in this regard, the present invention provides a compound comprising a bifunctional $^{225}$Ac-HEHA conjugated to a targeting agent as described above.

Also provided by the present invention is a method of attaching HEHA, which is not bifunctional, to a protein. See, for example, the method set forth in Example 11. Accordingly, the present invention further provides a HEHA-protein compound.

In another embodiment of the present invention, a method of making HEHA is provided. The method comprises preparing the free base of the macrocycle 1,4,7,10,13,16-hexaazacyclooctodecane under anhydrous conditions, azeotropically removing trace water with benzene, N-alkylating the macrocycle to produce the hexaester, saponifying the hexaester, and purifying HEHA. Preferably, the hexaester is produced by reacting the free base with $Na_2CO_3$ and tert-butyl bromoacetate in anhydrous $CH_3CN$. A preferred method is set forth in Example 1.

In the practice of the present invention, $^{225}$Ac can be chelated either before or after the chelator is conjugated to a targeting agent. The order chosen can take into account stability and other factors and is well within the ordinary skill in the art.

Methods of complexing metal ions with chelants are known and are within the level of ordinary skill in the art. A metal can be incorporated into a chelant moiety by one of three general methods, i.e., direct incorporation, template synthesis and/or transmetallation. Direct incorporation is preferred.

Generally, the metal is titrated from substoichiometric levels up to full incorporation, thus eliminating the need for dialysis and extensive chromatographic purification. In this manner, significant losses as well as dilution are avoided.

Generally, a water-soluble form of the metal, such as an inorganic salt, is dissolved in an appropriate volume of distilled, deionized water, preferably in a dilute acid medium having a pH of from about 1 to about 7 and most preferably at a pH of from about 4 to about 6. Ambient temperatures of about 20° C. to 27° C. or below (to just above freezing) can be readily employed with stirring for metal chelation. Any appropriate metal salt, either in solid form or in solution, can be contacted with the chelate, either free in solution or conjugated to a targeting agent, in order to form the chelated $^{225}$Ac. The pH of the mixture is raised slowly by addition of base, typically 0.1 M NaOH, until the donor groups of the polychelant are deprotonated, generally in the pH range of from about 5 to about 9, depending on the chelant moieties. Particular care must be taken to maintain the pH below 8 to avoid precipitation of the metal hydroxide. Preferred methods include those set forth in Examples 2 and 6.

A wide variety of metal salts can be employed including, for example, nitrates, iodides, chlorides, citrates, acetates and the like. The choice of an appropriate metal salt as well as the choice of a particularly appropriate chelate for any given metal is within the ordinary skill in the art. It will be apparent that the practice of this invention permits the processing of rather small quantities of metal and targeting agent to form metal chelate and metal chelate targeting agent conjugates. The amount of metal employed may be from trace amounts to amounts in excess of equimolar with the chelate.

In still yet another embodiment of the present invention, a method of making a bifunctional HEHA is provided. Preferred methods include those set forth in Example 3. The method comprises the preparation of a tert-butyloxycarbonyl protected iminodiacetic acid that is condensed with an amino acid ester. The resulting diester is then saponified with base, and after acidification, converted to a disuccinimidyl ester. This active diester is then reacted with an N-2-aminoethyl amide of para-nitrophenylalanine that introduces the latent bifunctionality aspect that will be unmasked. The protecting group is removed by treatment with acid, and the amide carbonyl functional groups are reduced via diborane. The resulting macrocyclic polyamine is isolated as the protonated salt. The free base is generated and then the free amines are alkylated to introduce protected R groups. The protected R groups are then deprotected. The nitro group is then hydrogenated to the aniline, which is then converted to an isothiocyanate, a haloacetamide or a maleimide for conjugation to a targeting agent.

The methods described are well-defined and understood and available to those skilled in the art. Choices of protecting groups, active esters, coupling reagents, and conjugation reactive groups are within the literature. See, for example, Bodanszky, *Principles of Peptide Synthesis*, 2$^{nd}$ Ed., Springer-Verlag, NY (1993); Green et al., *Protective Groups in Organic Synthesis*, 2$^{nd}$ Ed., John Wiley & Sons, Inc. (1991); Wong, *Chemistry of Protein Conjugation and Crosslinking*, CRC Press, Boca Raton, Fla. (1991); Lundblad, *Chemical Reagents for Protein Modification*, CRC Press, Boca Raton, Fla. (1991); and Magerstadt, *Antibody Conjugates and Malignant Disease*, CRC Press, Boca Raton, Fla. (1991).

Another route to prepare bifunctional HEHA reagents is via the preparation of the cyclic hexapeptide, wherein the amino acid components provide the latent bifunctionality aspect that will be unmasked, specifically an amino acid such as of para-nitrophenylalanine or an ε-protected lysine. The advantage to this method is the potential to introduce additional functional groups into the macrocyclic ring stereospecifically and thus tune the cavity size of the macrocycle. The ring is formed from the linear hexapeptide by cyclization with an activating and/or dehydrating reagent, for example DPPA (diphenylphosphoryl azide). The carbonyl functional groups are reduced via diborane. The free amines in the resulting macrocyclic polyamine are then alkylated to introduce protected R groups. The protected R groups are then deprotected. The nitro group is then hydrogenated to the aniline, which is then converted to an isothiocyanate, a haloacetamide or a maleimide for conjugation to a targeting agent. See, for example, Bodanszky (1993), supra; Green et al. (1991), supra; Wong (1991), supra; Lundblad (1991), supra; Magerstadt (1991), supra; and Aston et al., *Tetrahedron Lett.* 35:3687–3690 (1994).

If $^{225}$Ac-HEHA, wherein the HEHA is bifunctional, or the bifunctional HEHA is to be conjugated, $^{225}$Ac-HEHA or the bifunctional HEHA is mixed in aqueous solution with the desired targeting agent, such as an antibody, at a pH of from about 6 to about 11, most preferably at a pH of from about 7 to about 9.5. Desirably, the pH is adjusted with a buffered solution, such as a bicarbonate buffered solution. Once again, the choice of an appropriate buffer is within the ordinary skill in the art. The temperature of the solution can range from just above freezing to the temperature at which the chelate becomes unstable or the protein denatures. Often temperatures above 37° C. tend to denature proteins. Generally, chelate and targeting agent are mixed in a molar ratio of greater than 1:1 and less than 100:1 depending on protein concentration. Ratios of about 2:1 to about 4:1 are preferred, but the choice of reaction conditions is within the ordinary skill in the art.

Accordingly, in still yet another embodiment of the present invention, a method of attaching a bifunctional HEHA to a targeting agent is provided. The method comprises the conjugation of a bifunctional HEHA to a targeting agent or vector. Preferred methods include those set forth in Example 4. In one particular embodiment, the targeting agent was a monoclonal antibody. The antibody was prepared for conjugation by transfer of the antibody by dialysis to the conjugation buffer (bicarbonate, 0.5 M EDTA, pH=8.0). After dialysis, the concentration was determined spectrophotometrically. To the antibody solution, a solution of a bifunctional HEHA in water was added. Typical initial ratios used to achieve the desired final chelate/protein ratio of 1–2 were a 10-fold initial excess of ligand for whole antibodies and a 10–15-fold initial excess of ligand for antibody fragments. After the conjugation reaction was completed (18 hr), the reaction mixture was purified by centrifugation filtration. The buffer was changed to ammonium acetate buffer (0.15 M, pH=7.0) by centrifugation filtration. Alternately, dialysis against 1 l of 0.15 M NH$_4$OAc for a minimum of 6 hr and changing buffer for a total of 4 times provided the conjugate ready for radiolabeling.

The conjugates can be used as such with appropriate pH adjustment, if needed. Alternatively, if it is desired to purify the conjugate from unconjugated chelate or products of any side reactions, the product can be purified. A variety of standard purification techniques known in the art can be used, including column chromatography and high performance liquid chromatography (HPLC).

$^{225}$Ac-HEHA and conjugates thereof can be administered in vivo in the form of a composition, e.g., a pharmaceutical composition, comprising a carrier, e.g., pharmaceutically acceptable carrier. A biologically acceptable, normal saline solution can be appropriately employed. The carrier can include a minor amount of a carrier protein, such as human serum albumin, for example, to stabilize the targeting agent. Stabilizers, antioxidants, osmolality adjusting agents, buffers, pH adjusting agents, etc., can be included in the composition. The composition can be in the form of a solution, suspension or dispersion. Suitable additives include, for example, physiologically biocompatible buffers, additions of chelants or calcium chelate complexes, or optionally, additions of calcium or sodium salts.

Parenterally administrable forms, e.g., intravenous forms, should be sterile and free from physiologically unacceptable agents and should have low osmolality to minimize irritation or other adverse effects upon administration. Suitable vehicles include aqueous vehicles customarily used for administering parenteral solutions, such as sodium chloride injection, Ringer's injection, dextrose injection, dextrose and sodium chloride injection. Lactated Ringer's injection and other solutions are as described in *Remington's Pharmaceutical Sciences*, 15$^{th}$ ed., Easton: Mack Publishing Co. (1975). The solutions can contain preservatives, antimicrobial agents, buffers and antioxidants conventionally used for parenteral solutions, excipients and other additives that are compatible with the chelates and will not interfere with the manufacture, storage or use of products.

The concentration of $^{225}$Ac-HEHA or conjugate thereof in a composition will be a matter of choice. Levels of 0.5 mg/ml are readily attainable but the concentration may vary considerably depending upon the specifics of any given application. Appropriate concentrations of biologically active materials in a carrier are routinely determined in the art.

The effective dose (referred to herein as "disease-treatment effective amount," "cancer-treatment effective amount," "tumor-treatment effective amount," "decontaminating effective amount" and "detoxifying-effective amount") of HEHA, $^{225}$Ac-HEHA or conjugate of either of the foregoing to be utilized for any application will also depend upon the particulars of that application. In treating tumors in the context of radioimmunotherapy, for example, the dose will depend, inter alia, upon tumor burden, accessibility, route of administration, administration of other active agents, and the like. Generally, a therapeutically effective dose is from about 20 mCi to about 300 mCi.

HEHA and $^{225}$Ac-HEHA-targeting agent can be administered in accordance with the present inventive methods by any suitable route. Such routes include intravenous, intraperitoneal, and the like, depending on the site of contamination with $^{224}$Ac or the disease or cancer to be treated, respectively, the location of the contaminated/diseased/cancerous cells, the extent of contamination/disease/cancer, and other factors. The determination of the appropriate route(s) of administration for a given application is within the ordinary skill in the art. In the treatment of prostate cancer, for example, transurethral delivery to the prostate or periprostate space or transrectal injection can be used.

In the context of radioimmunotherapy, the conjugates of the present invention are introduced into the body and are allowed to concentrate in the target region. The therapeutic effect occurs when the conjugates are near or in contact with and bind to the targeted cells. Cell death can be a direct or indirect result of the radiation event of the radiometal that is positioned in close proximity to the cell. Desirably, the conjugate comprises a monoclonal antibody that is specific (e.g., for a cell-surface molecule) for a cell, such as a diseased cell, to be killed. Cell death is caused by decay of the radiometal and can occur in one of two ways. First, if the alpha particle is emitted in the direction of the diseased cell, a single hit in the cell nucleus can be cytotoxic. The isotope to which the radiometal decays after emitting the alpha particle is ejected from the chelate on a trajectory opposite that of the alpha particle. The bound cell, therefore, can still be hit even when the alpha particle is emitted on a trajectory away from the cell. A single hit in the cell membrane by the decayed isotope can cause irreparable cell injury leading to cell death. The relatively high effectiveness of the alpha particle means that less radioactive material can be employed. Selectivity of the targeting agent, e.g., monoclonal antibody, and the short range (a few cell diameters) of the alpha particles minimizes the destruction of healthy tissue on a cellular level.

The benefits that inure to this embodiment of the invention are numerous. The high specificity of the conjugate minimizes total radiation dosage. Only enough radiation for the target cells need be employed. In addition, $^{225}$Ac-HEHA is cleared rapidly from the body should the targeting agent be disrupted. Additionally, since the amount of radiometal employed is minimized, the radiation hazard to persons preparing and administering the conjugate is significantly reduced. In addition, tissue damage or whole body dose during therapy is markedly reduced as compared to that from presently employed methods of radiation therapy, such as isotope implants, external radiation therapy, and immunoradiotherapy employing iodine-131 labeled polyclonal or autologous antibodies. Additionally, both biological and physical half-lives of the targeting radiobiological can now be controlled, minimizing whole body radiation effects. Since radiation is targeted to specific cell types, such as neoplastic cells, a therapeutic dose is delivered specifically to malignant cells, either localized or metastasized. The ability of conjugates to provide an effective dose of therapeutic radiation specifically to metastasized cells is also unique and singularly useful for cancer therapy. Desirably, when the cancer is a solid tumor, $^{225}$Ac-HEHA or $^{225}$Ac-HEHA-targeting agent is administered intratumorally. Any leakage of decay products to the surrounding healthy tissue can be chelated by the subsequent or simultaneous administration of HEHA or the like. Desirably, a $^{225}$Ac-HEHA-targeting agent that targets leukemic cells or prostate cancer cells is administered in the treatment of leukemia or prostate cancer, respectively. The $^{225}$Ac-HEHA-targeting agent desirably is internalized by the cell and all decay occurs within the cell, preferably with the daughter isotopes decaying thereafter within one hour or less, thereby minimizing any damage to normal cells and tissue.

In view of the above, the present invention provides a method of treating disease. The method comprises administering to a patient having disease a disease-treatment effective amount of $^{225}$Ac-HEHA-targeting agent in which the targeting agent is specific for diseased cells. Preferably, the targeting agent is an antibody.

Also provided is a method of treating cancer. The method comprises administering to a patient having cancer a cancer-treatment effective amount of $^{225}$Ac-HEHA-targeting agent in which the targeting agent is specific for the cancer. Preferably, the targeting agent is an antibody. If the cancer is a solid tumor, the method preferably comprises intratumorally administering to a patient having a tumor a tumor-treatment effective amount of $^{225}$Ac-HEHA or $^{225}$Ac-HEHA-targeting agent, in which the targeting agent is specific for the tumor. Any leakage of decay products to the surrounding healthy tissue can be chelated by the subsequent or simultaneous administration of HEHA or the like.

A method of decontaminating a sample from $^{225}$Ac is also provided. The method comprises contacting the sample with a decontaminating-effective amount of HEHA. A decontaminating-effective amount can be determined in accordance with methods known in the art. Preferably, the HEHA is attached to a solid support and the sample is a liquid. This method has application in the context of bioremediation.

Further provided is a method of decontaminating a person who has been externally contaminated with $^{225}$Ac. The method comprises contacting the person with a decontaminating-effective amount of HEHA. A decontaminating-effective amount can be determined in accordance with methods known in the art. Similarly, a method of detoxifying a person who has internalized $^{225}$Ac is also provided. The method comprises administering to the person a detoxifying-effective amount of HEHA. A detoxifying-effective amount can be determined in accordance with methods known in the art.

EXAMPLES

The following examples serve to illustrate further the present invention and are not intended to limit its scope in any way. With respect to the following examples, 1,4,7,10,13,16-hexaazacyclooctodecane trisulfate (hexacyclen trisulfate) was purchased from Aldrich (Milwaukee, Wis.) and tert-butyl bromoacetate was purchased from Fluka (Ronkonkoma, N.Y.). All other reagents were purchased from Aldrich, Sigma (St. Louis, Mo.) or Fluka and were used without further purification.

Chromatography was performed on silica gel 60, 220-440 mesh ASTM (Fluka). Thin-layer chromatography (TLC) was performed on silica gel 60 F-254 plates (EM Reagents). All glassware used in the synthesis of the ligands after ester hydrolysis was acid-washed and rinsed with distilled deionized water.

$^1$H and $^{13}$C NMR were obtained using a Varian Gemini 300 instrument at ambient temperature. Chemical shifts were reported in ppm on the scale relative to tetramethylsilane (TMS), trimethylsilyl propionic acid-D$_5$-Na salt (TSP) or solvent. Proton chemical shifts are annotated as follows: ppm (multiplicity, integral, coupling constant (Hz)). Chemical ionization mass spectra (CI-MS) were obtained on a Finnegan 3000 instrument (Finnegan, San Jose, Calif.). Fast atom bombardment mass spectra (FAB-MS) were obtained using an Extrel 400 instrument. High resolution FAB (HR-FAB) mass spectra were obtained on a JEOL SX102 mass spectrometer operated at an accelerating voltage of 10 kV. Samples were desorbed from a glycerol matrix uing 6 keV xenon atoms. Mass measurements in HR-FAB were performed at 10,000 resolution. Analytical HPLC was performed on a Beckman gradient system equipped with Model 114M pumps controlled by System Gold software and a Model 165 dual wavelength detector set at 254 and 280 nm. An Altex ODS C18 column (4.6 mm×15 cm) with a 25 min gradient of 100% aqueous 0.05 M triethylammonium acetate to 100% methanol at a flow rate of 1 ml/min was used. Infrared spectra were obtained using a Bio-Rad FTS-45 spectrophotometer with the samples prepared as Nujol mulls.

HPLC purification of $^{225}$Ac conjugates, as well as HPLC analysis of samples from serum stability studies, were performed employing a Dionex system equipped with a Model GPM-2 gradient pump, a Gilson Model 112 UV monitor operating at 280 nm, an IN/US γ-RAM flow-through radioactivity detector, and a Gilson Model 203 fraction collector. The size exclusion HPLC column (TSK-Gel® G3000SW, TosoHaas, Japan) eluted with PBS, pH 7.2, at 1 ml/min was used for these separations. Radioactive samples were counted in a Minaxi γ-counter (Packard Instrument Company).

Example 1

This example describes the synthesis of 1,4,7,10,13,16-hexaazacyclooctodecane-N,N',N'',N''',N'''',N'''''-hexaacetic acid (HEHA).

1,4,7,10,13,16-hexaazacyclooctodecane trisulfate was converted to the free base ([18]aneN$_6$) by neutralizing the trisulfate salt to pH>13 with sodium hydroxide, removing water in vacuo, adding benzene, refluxing the resultant slurry with a Dean-Stark trap (Kontes Glassware Co., Vineland, N.J.) for 4–6 hrs to remove residual water, filtering the benzene solution, and evaporating to dryness to yield the free base. The hexaester, 1,4,7,10,13,16-hexakis(tert-butoxycarbonylmethyl)-1,4,7,10,13,16-hexaazacyclooctadecane, was prepared by adding Na$_2$CO$_3$ (2 g, 19.4 mmol, 10 eq) and tert-butyl bromoacetate (2.3 ml, 15.5 mmol, 8 eq) to a solution of [18]aneN$_6$ (500 mg, 1.95 mmol, 1 eq) in anhydrous CH$_3$CN (25 ml). The reaction was stirred at room temperature under inert atmosphere and monitored by $^1$H NMR. The reaction was completed in seven days. The solvent was removed under vacuum, a minimum volume of CHCl$_3$ was added to generate a slurry, the slurry was filtered through Celite-577 (Fluka) and the eluant was applied to a silica column (5 cm×20 cm). The column was eluted with a 0–10% methanol/CHCl$_3$ gradient and fractions were collected. Fractions were analyzed by thin layer chromatography (TLC) on silica developed with 10% methanol/CHCl$_3$ and viewed by I$_2$ staining. Fractions containing the product were combined and concentrated to yield 1.2 g (65%) of hexaester as a white solid. $^1$H NMR (300 MHz, CDCl$_3$/TMS) δ 3.36 (s, 12H, NCH$_2$CO); 2.78 (s, 24H, NCH$_2$CH$_2$N); 1.45 (s, 54H, C(CH$_3$)$_3$; $^{13}$C NMR (75.5 MHz, CDCl$_3$) δ 171.35; 80.58; 55.39; 51.74; 28.13.

HEHA was prepared by heating the hexaester (1.1 g, 1.17 mmol)in 12 M HCl (10 ml) at 105° C. for 5 hr. The reaction mixture was cooled and the volume was reduced under vacuum until a precipitate formed. The mixture was chilled and the product was collected by filtration to yield 700 mg (73%) of HEHA as the hexahydrochloride salt. All spectra agreed with the literature values (Kimura et al., *Chem Pharm Bull*, 33: 655–661 (1985)). $^1$H NMR (300 MHz, D$_2$O) δ 3.58 (s, 12H, N—CH$_2$—CO); 3.34 (s, 24H, N—CH$_2$CH$_2$—N).

Example 2

This example describes the radiolabeling of HEHA with $^{225}$Ac.

$^{225}$Ac was separated from $^{225}$Ra (t$_{1/2}$=15 days) by ion exchange and extraction column chromatography as described previously (Boll et al. (1997), supra). Stock solutions of purified $^{225}$Ac in 0.1 M HNO$_3$ were freshly prepared as needed. $^{225}$Ac was complexed with HEHA by mixing approximately 100 μl of $^{225}$Ac solution (approx. 10 MBq, 0.1 M HNO$_3$) with 20 μl of ligand (approx. 1.0×10$^{-2}$ M in H$_2$O) and adjusting the pH to near 5.0 by the addition of 5–10 μl of 1.0 M NH$_4$OAc. The mixture was kept at 40° C. for 30 min and then purified on a Chelex column (Bio-Rad Laboratories, Richmond, Calif.); approx. 300 μl bed volume, pre-equilibrated with 0.1 M NH$_4$OAc, pH=5.0), using 2 ml of NH$_4$OAc solution as eluant.

Example 3

This example describes the synthesis of bifunctional HEHA.

Boc-IDA-diglycine Ethyl Ester

N-tert-butyloxycarbonyl-iminodiacetate (Boc-IDA) (20 g, 85.8 mmol, 1 eq), glycine ethyl ester hydrochloride (24 g, 171.9 mmol, 2 eq) and triethylamine (24 ml, 172 mmol)

were dissolved in anhydrous N,N-dimethylformamide (DMF) (700 ml). 1-ethyl-3-(3-dimethyl-aminopropyl) carbodiimide (EDC) (34 g, 88.7 mmol, 2.1 eq) was added and the solution stirred for 18 hrs at room temperature. The DMF was removed under vacuum and the residue was dissolved in ethyl acetate (600 ml). The ethyl acetate was extracted with water (200 ml×1); 5% NaHCO$_3$ (200 ml×3); brine (200 ml×1); 1 M HCl (200 ml×1) and brine (200 ml×2). The organic layer was dried over Na$_2$SO$_4$, filtered and concentrated to yield an oil (23 g, 66%). $^1$H NMR (DMSO (dimethyl sulfoxide)-d$_6$) δ: 1.19 (t, 6H, CH$_3$); 1.35 (s, 9H, C(CH$_3$)$_3$); 3.30 (s, 2H, CH$_2$); 3.32 (s, 2H, CH$_2$); 3.88 (s, 2H, CH$_2$); 3.91 (s, 2H, CH2); 4.08 (q, 4H, CH$_2$CH$_3$); 8.80 (t, 2H, NH); $^{13}$C NMR (DMSO-d$_6$) δ 14.01, 27.73, 51.29, 21.77, 60.46, 79.76, 154.87, 169.86, 170.29, 170.41; MS (CI/N$_3$) m/e 404 (M$^+$+1). Anal. calcd for C$_{17}$H$_{29}$N$_3$O$_8$: C, 50.62; H, 7.24; N, 10.42. Found: C, 50.09; H, 7.10; N, 10.13.

Boc-IDA-diglycine

To a stirred solution of NaOH (5.2 g, 131 mmol, 2.3 eq) in ethanol (200 ml) and H$_2$O (100 ml) was added dropwise BOC-IDA diglycine ethyl ester (23 g, 57 mmol, 1 eq) in ethanol (200 ml). The solution was stirred 60 hours at room temperature followed by removal of ethanol under vacuum. The residual aqueous layer was extracted with ethyl acetate (200 ml×1). The aqueous layer was chilled to 0° C. and acidified to pH 2 with 3 M HCl (~50 ml). To facilitate extraction, 20 g NaCl were added and the aqueous layer was extracted with ethyl acetate repeatedly. The product began to precipitate in the organic layer and the organic layer was heated to maintain a clear solution before drying with sodium sulfate. After drying and filtration, concentration of the organic layer yielded the pure product as a white solid (14.59 g, 74%). The product was dried under vacuum at 70° C. for 24 hours. $^1$H NMR (DMSO-d$_6$) δ: 1.34 (s, 9H, C(CH$_3$)$_3$); 3.79 (s, 2H, CH$_2$); 3.80 (s, 2H, CH$_2$); 3.84 (s, 2H, CH$_2$); 3.90 (s, 2H, CH2); 8.75 (m, 2H, NH); $^{13}$C NMR (DMSO-d$_6$) δ 27.79, 51.47, 51.96. 79.76, 154.99, 170.29, 171.26; MS (CI/NH$_3$) m/e 348 M$^+$+1); Anal. calcd for C$_{13}$H$_{21}$N$_3$O$_8$·HCl; C, 40.69; H, 5.77; N, 10.95. Found: C, 41.17; H, 5.61; N, 11.03.

BOC-IDA-diglycine Disuccinimidyl Ester

Thoroughly dried Boc-IDA-diglycine (14 g, 40.3 mmol, 1 eq) and N-hydroxysuccinimide (10.2 g, 88.7 mmol, 2.2 eq) were stirred in DMF (250 ml) under argon. EDC (17 g, 88.7 mmol, 2.2 eq) was added and the solution was stirred for 18 hrs. The DMF was removed under vacuum and the residue was dissolved in ethyl acetate (600 ml). The organic layer was extracted with water (150 ml×1); 5% NaHCO$_3$ (200 ml×3); brine (200 ml×1); and brine (200 ml×2). The organic layer was dried with Na2SO$_4$, filtered and concentrated to yield a white solid (15.86 g, 73%). The product was thoroughly dried under vacuum at 70° C. prior to use in cyclization. $^1$H NMR (DMSO-d,) δ: 1.34 (s, 9H, C(CH$_3$)$_3$); 2.82 (s, 8H, succinimide); 3.88 (s, 2H, CH$_2$); 3.94 (s, 2H, CH$_2$); 4.31 (s, 2H, CH$_2$); 4.33 (s, 2H, CH$_2$); 8.95 (t, 2H, NH); $^{13}$C NMR (DMSO-d$_6$) δ 25.19, 25.43, 27.74, 51.05, 79.89, 154.87, 166.53, 170.23, 170.54; MS (CI/NH3) m/e 542 (M$^+$+1). Anal. calcd for C$_{21}$H$_{27}$N$_5$O$_{12}$·1.5H$_2$O: C, 44.37, H, 5.31; N, 12.32. Found: C, 44.43; H, 5.54; N, 11.48.

1-(tert-Butoxycarbonyl)-8-(4-nitrobenzyl)-3,6,9,14, 17-pentaoxo-1,4,7,10,13,16-hexaazacyclooctodecane In a 5 liter 3-necked Morton flask, anhydrous dioxane (3.5 l) was heated to ~90° C. BOC-IDA-diglycine disuccinimidyl ester (5.42 g, 10 mmol) in DMF (50 ml) and N-(2-aminoethyl)-4-nitrophenylalaninamide (2.52 g, 10 mmol) in DMF (50 ml) were each loaded in 50 ml gas-tight syringes and added to the dioxane so that the addition was complete after 24 hr. Second and third additions were 10 mmol and 5.5 mmol in each reactant, respectively. After the third addition, the reaction was heated for an additional 18 hr and then cooled to room temperature. The reaction was concentrated to a thick brown oil under vacuum and the residue was dissolved in chloroform (500 ml). The chloroform was washed with water (1×200 ml), 5% NaHCO$_3$, (2×200 ml), brine (1×200 ml), 1 M HCl (2×200 ml), brine (1×200 ml) and water (1×100 ml). A sticky brown residue stuck to the inside of the separatory funnel was dissolved in methanol (MeOH) and reduced to dryness. The CHCl$_3$ layer was kept separate and reduced to dryness. The residues isolated from the CHCl$_3$ and MeOH were each chromatographed on short silica gel columns with 10–20% MeOH in CHCl$_3$. Fractions that contained the product were combined. This product was purified by column chromatography on silica gel eluted with a 10–20% MeOH in CHCl$_3$ gradient yielded the pure macrocycle as a tan solid (2.55 g, 19%). $^1$H NMR (DMSO-d6) δ: 1.33 (s, 9H, C(CH$_3$)$_3$), 2.8–4.0 (overlapping multiplets, 14H); 4.5 (m, 1H, CH); 7.47 (s, 2H, Ar); 7.58 (t, 0.5H, NH); 7.74 (d, 1.5H, NH); 7.96 (d, 1H, NH); 8.12 (d, 2H, Ar); 9.14 (t, 0.5H, NH); 9.21 (m, 1H, NH); 9.36 (t, 0.5H, NH); $^{13}$C NMR (DMSO-d,) δ 627.74, 52.15, 53.36, 53.54, 79.22, 80.13, 123.36, 130.65, 146.37, 146.56, 154.69, 169.20, 170.66, 171.08, 171.27, 171.69; MS (CI/NH$_2$) m/e 564; (M$^+$+1) HPLC t$_R$=18.7 min; Anal. calcd for C$_{24}$H$_{33}$N$_7$O$_9$·2H$_2$O: C, 48.08; H, 6.21; N, 16.35. Found: C, 48.28, H, 5.73; N, 15.87.

Hexa-tert-butyl 2-(4-nitrobenzyl)-1,4,7,10,13,16-hexaazacyclooctodecane-1,4,7,10,13,16-hexaacetate Dioxane (50 ml) in a 250 ml 3-necked round bottom flask was chilled in an ice bath and saturated with HCl(g) for 2 hr. 1-(tert-butoxycarbonyl)-8-(4-nitrobenzyl)-3,6,9,14,17-pentaoxo-1,4,7,10,13,16-hexaazacyclooctodecane (1.66 g, 3 mmol) was added and HCl (g) was bubbled through the reaction mixture for 1 hr. The reaction was stirred overnight (18 hr) at room temperature. Diethyl ether (200 ml) was added and the reaction mixture chilled in the freezer for 6 hr. The yellow precipitate was collected on a Buchner, washed with diethyl ether, and vacuum-dried overnight. The product was a pale yellow solid (1.9 g).

$^1$H NMR (DMSO-d$_6$) δ 3.0–3.3 (m, 7H), 3.4 (m, 2H), 3.70 (m, 3H), 3.89 (m, 3H), 4.44 (m, 1H—CH—Ar), 7.54 (d, 2H, Ar), 7.80 (t, 1H, NH), 8.05 (t, 1H, NH), 8.14 (d, 2H, Ar), 8.20 (d, 1H, NH), 8.96 (d of t, 2H, NH); MS (CI/NH$_3$) m/e 464 (M$^+$+1); HPLC t$_R$=15.3 min; Anal. calcd for C$_{19}$H$_{25}$N$_{77}$·HCl·dioxane: C, 44.92; H, 6.06; N, 15.94. Found: C, 44.23; H, 5.90; N, 15.97.

The above deprotected product (1.8 g, 3.0 mmol) and anhydrous tetrahydrofuran (THF) (50 ml) were combined in a 100 ml 2-necked round bottom flask-and chilled in an ice bath. To this was added 1 M borane in THF (5–6 ml). The mixture was allowed to warm to room temperature and then heated at 50° C. Over three days additional 1 M borane in THF was added in 15, 5, and 10 ml portions, respectively, for a total of 36 mmol. The reaction mixture was evaporated to dryness and the yellow solid (1.55 g) was vacuum-dried. This residue was transferred to a 250 ml 3-necked flask and absolute ethanol (EtOH) (80 ml) was added. HCl(g) was bubbled through the reaction mixture for 2 hr and then the reaction was heated at reflux for 17 hr. Afterwards, the reaction mixture was cooled to room temperature, diethyl ether (Et$_2$O) (150 ml) was added and the suspension was placed in the freezer overnight. The pale yellow precipitate was collected by suction filtration, washed with diethyl ether and vacuum-dried (1.01 g, 54%).

$^1$H NMR (D$_2$O pH 1–2) δ 3.0–4.0 (m, 25H, macrocycle, CH2Ar), 7.5 (m, 2H, Ar), 8.25 (m, 2H, Ar); MS (CI/NH$_3$) m/e 394 (M$^+$+1); HPLC t$_R$=17.8 min; Anal. calcd for C$_{19}$H$_{35}$N$_7$O$_2$·6HCl·H$_2$O: C, 36.21; H. 6.87, N, 15.56. Found: C, 36.06; H, 6.80; N, 14.59.

The above reduced product hexamine hexahydrochloride (502 mg) was taken up in water (4 ml) and the pH was raised to 13 with NaOH pellets to generate the free base, 2-(4-NO$_2$-Bz-[18]ane N6). The aqueous solution was extracted with CHCl$_3$ (4×100 ml). The combined CHCl$_3$ layers were dried over anhydrous Na$_2$SO$_4$ and the drying agent was filtered. The free base was isolated as a yellow solid (539 mg, 80% recovery) after evaporation of the filtrate. $^1$H NMR (CDCl$_3$) δ 1.6 (br, 6H, NH); 2.2–3.4 (m, 25H, macrocycle, CH$_2$Ar), 7.3 (m, 2H, Ar), 8.05 (m, 2H, Ar); $^{13}$C NMR (CDCl$_3$) δ 38.39, 38.81, 46.34, 48.34, 48.53, 48.77, 49.07, 49.38, 52.41, 52.78, 58.67, 123.32, 123.57, 129.94, 146.34, 147.55. The free base 2-(4-NO$_2$-Bz-[18]ane N6) (59.3 mg, 1.51 mmol) was dissolved in anhydrous DMF (10 ml) and tert-butyl bromoacetate (1.78 g, 9.1 mmol) was added. The reaction was allowed to stir in an ice-bath and then warmed to room temperature for over 1 hr. An aqueous solution of Na$_2$CO$_3$ (965 mg in 20 ml H$_2$O) was added and the mixture was stirred for 2.5 hr. Toluene (10 ml) was added and the reaction mixture was stirred overnight (17 hr). The reaction mixture was poured into a separatory funnel and the aqueous layer was drained. The toluene layer was saved. The aqueous layer was extracted with CHCl$_3$ (2×100 ml) and the combined CHCl$_3$ and toluene layers were reduced to dryness. The residue was determined to contain hexa-tert-butyl ester product by mass spectrometry. The product was purified from the residue on two consecutive silica gel columns (2×10 cm) with a gradient from 5–10% MeOH in CHCl$_3$ and finally 10% NH$_3$(aq) in MeOH. Early fractions contained the hexa-tert-butyl ester product with some impurity. Later fractions contained only the hexa-tert-butyl ester product. These were combined, reduced to dryness and vacuum dried (462 mg, 29%).

$^1$H NMR (CDCl$_3$) δ 1.45 (overlapping s, 54H, tBu); 2.8–3.4 (m, 37H, macrocycle, CH$_2$Ar), 7.46 (d, 2H, Ar), 8.13 (d, 2H, Ar); $^{13}$C NMR (CDCl$_3$) δ 27.94, 52.05, 53.32, 55.33, 55.63, 55.99, 80.58, 123.20, 130.25, 146.21, 149.37, 170.93, 171.65; MS (CI/NH$_3$) m/e 1078.6 (M$^+$+1), 1100.6 (M$^+$+Na); Anal. calcd for C$_{55}$H$_{94}$N$_7$O$_{14}$·0.5H$_2$O: C, 60.81; H. 8.81; N, 9.03. Found: C, 58.97; H, 8.44; N, 9.01.

2-(4-Nitro-benzyl)-1,4,7,10,13,16-hexaazacyclooctodecane-1,4,7,10,13,16-hexaacetic Acid To a 10 ml round-bottomed flask hexa-tert-butyl 2-(4-nitrobenzyl)-1,4,7,10,13,16-hexaazacyclooctodecane-1,4,7, 10,13,16-hexaacetate (166 mg, 0.15 mmol) was combined with conc. HCl (5 ml) and heated at reflux for 6 hr. The HCl (aq) was removed by rotary evaporation and the residue was taken up in water (1–2 ml) and was lyophilized to give hexa-acid as a pale yellow solid (100 mg, 70%).

$^1$H NMR (D$_2$O, pH 1–2) δ 2.8–4.2 (m, 37H), 7.48 (br, 2H, Ar), 8.14 (br, 2H, Ar); MS (CI/NH$_3$) m/e 742 (M$^+$+1); HPLC t$_R$=10.5 min; Anal. calcd for C31H$_{47}$N$_7$O$_{14}$·6HCl: C, 38.95; H, 5.59; N, 10.26. Found: C, 39.12; H, 5.66; N, 10.49.

2-(4-Aminobenzyl)-1,4,7,10,13,16-hexaazacyclooctodecane-1,4,7,10,13,16-hexaacetic Acid A Schlenk flask was charged with 10% Pd/C (23.5 mg) and H$_2$O (3 ml) and fitted onto an atmospheric hydrogenator. The apparatus was flushed with H$_2$(g) two times to saturate fully the catalyst. A solution of 2-(4-nitrobenzyl)-1,4,7,10, 13,16-hexaazacyclooctodecane-1,4,7,10,13,16-hexaacetic acid (76.6 mg, 0.080 mnol) in water (3 ml) was injected via syringe into the flask. The hydrogenation was allowed to proceed until the uptake of H$_2$(g) ceased. The reaction mixture was filtered through a bed of Celite 577 packed in a medium glass fritted funnel. The filtrate was reduced to dryness by rotary evaporation and the residue was taken up in water (1–2 ml), which was then lyophilized to give the aniline as a pale yellow solid (56 mg, 75%).

$^1$H NMR (D$_2$O, pH 1–2) δ 2.6–4.2 (m, 37H), 7.46 (m, 4H, Ar); $^1$H NMR (D$_2$O, pH 13) δ 2.0–4.6 (m, 37H), 6.83 (m, 2H, Ar), 7.09 (m, 2H, Ar); MS (CI/NH3) m/e 712 (M$^+$+1); HPLC t$_R$=8.6 min; M–H$^+$ calcd for C$_{31}$H$_{48}$N$_7$O$_{12}$ 710.3371 found [HRFAB] m/e=710.3397, error +5.0 ppm.

2-(4-Isothiocyanatobenzyl)-1,4,7,10,13,16-hexaazacyclooctodecane-1,4,7,10,13,16-hexaacetic Acid (HEHA-NCS)

A 1 M solution of SCCl$_2$ in CHCl$_3$ (50 ml) was added to 2-(4-aminobenzyl)-1,4,7,10,13,16-hexaazacyclooctodecane-1,4,7,10,13,16-hexaacetic acid (30.5 mg) dissolved in H$_2$O (0.5 ml) in a vial. The mixture was stirred rapidly for 2 hr at room temperature. The aqueous layer was decanted with a pipet into a round-bottomed flask and the CHCl$_3$ layer was washed with H$_2$O (3×0.5 ml). The combined aqueous portions were reduced to approximately 1–2 ml by rotary evaporation. The solution was then lyophilized to give the isothiocyanate as a pale yellow solid (30.9 mg, 96%).

$^1$H NMR (DMSO-d6, pH 1–2) δ 3.0–4.0 (m, 37H), 7.33 (br, 4H, Ar); $^1$H NMR (D$_2$O, pH 13) δ 2.2–3.4 (m, 37H), 7.3 (m, 4H, Ar); MS (FAB/glycerol) m/e 754 (M$^+$+1); IR (Nujol) 2034.1 cm$^{-1}$; HPLC t$_R$=14.95 min; M–H$^+$ calcd for C$_{32}$H$_{46}$N7O$_{12}$S found [HRFAB] m/e=752.2971, error=+6.1 ppm.

Example 4

This example describes the attachment of a bifunctional HEHA to a targeting agent.

Preparation of Buffers

10× Conjugation Buffer 80.44 g NaHCO$_3$, 4.50 g Na$_2$CO$_3$ and 175.32 g NaCl were dissolved in deionized water (2 liter). The solution was passed through a column of Chelex-100 (1×7 in.) (Bio Rad, Na$^+$ form, 200–400 mesh), previously washed with water until neutral and equilibrated with the 10× buffer (200 mL).

30× Ammonium Acetate Buffer

5M NH$_4$OAc buffer was passed through a column of Chelex-100 (1×7 in.) (Bio Rad, Na$^+$ form, 200–400 mesh), previously washed with water until neutral and equilibrated with the 30× buffer (200 ml).

Materials

Spectra/Por CE DispoDialysers MWCO=10,000 (Fisher)—or use an equivalent type dialysis tubing with appropriate MWCO.
Amicon Centricon Concentrators Conjugation Procedure Transfer antibody solution to dialysis tubing and dialyze against 1× conjugation buffer (1 l) for 6 h at 4° C. (Prepare by combining the 10× conjugation buffer (100 ml) with 0.5 M EDTA, pH=8.0 (10 ml) and dilute to 1 L with deionized water to obtain the 1× buffer.). After dialysis, the concentration is determined spectrophotometrically. To the antibody solution, add a solution of ligand in water. Typical initial ratios used to achieve the desired final chelate/protein ratio of 1–2 are a 10-fold initial excess of ligand for whole antibodies and a 15-10-fold initial excess of ligand for fragments. The reaction mixture is allowed to stand at room temperature overnight (18 hr). The reaction mixture is transferred to Centricon filtration units, with the appropriate MW cut-off, so that each unit contains no more than 3 mg of antibody. Ammonium acetate buffer (0.15 M, pH=7.0, prepared from the 30× stock) is added to a total volume of 2–2.5 ml and the filtration units are centrifuged to approximately 0.5 ml. Add more 0.15 M ammonium acetate buffer and repeat this process for a total of 6 times. If the antibody tends to stick to the Centricon units (possibly in the case of antibody fragments), dialysis against 1 l of 0.15 M NH4OAc for a minimum of 6 hr and changing buffer for a total of 4 times is routine.

Example 5

This example describes the attachment of a bifunctional HEHA to a monoclonal antibody.

Purified monoclonal antibody CC49 (Murano et al., *Cancer Research* 48:4588–4596 (1988)), which reacts with the human pancarcinoma antigen TAG-72, and its isotype-match BL-3 (Colcher et al., *Cancer Research* 47: 4218–4224 (1987)) were supplied by Dr. J. Schlom, (Laboratory of Tumor Immunology and Biology, NCI, NIH); TIOl antibody (Carrasquillo et al., *Antibody, Immunocon., Radiopharm.* 6:111–126 (1993)) was furnished by Dr. J. Carrasquillo (Nuclear Medicine Department, Clinical Center, NIH).

Antibody solutions were initially transferred to dialysis tubing (Spectra/Por CE DispoDialysers, MWCO 10K, 5 ml) and were dialyzed against conjugation buffer, (1 l, 0.05 M $CO_3^{-2}/HCO_3^{-1}$, 0.15 M NaCl, 5 mM EDTA, pH 8.6) for 6 hr at 4° C. After dialysis, the protein concentration was determined spectrophotometrically. Extinction coefficients of 1.4, 0.65 and 1.3 ml/mg cm were determined for mAb's BL-3, CC49 and T101, respectively, based on an mAb concentration from a protein determination using the Lowry method (Lowry et al., *J. Biol. Chem.* 193: 265–275 (1951)) with a bovine serum albumin standard. A solution of HEHA-NCS in water was added to the antibody solution, such that initial molar ratio of ligand to antibody was 50-fold. The reaction mixture was allowed to stand at room temperature overnight (18 hr). The reaction mixture was transferred to Centricon (MWCO 30K or 50K) (Amicon) filtration units. Ammonium acetate buffer (0.15 M $NH_4OAc$, pH 7.0) was added to the filtration unit to a total volume of 2–2.5 ml and the filtration units were centrifuged until the remaining volume was approximately 0.5 ml. Additional buffer was added and this process was repeated for a total of 6 times. The final antibody concentration was measured spectrophotometrically and the ligand to protein ratio (L/P) was determined as previously described (Dadachova et al., *Nucl. Med. Biol.* 26: 977–982 (1999)).

Example 6

This example describes the radiolabeling of a HEHA-targeting agent with [225]Ac.

A slightly modified procedure of that described in detail in Mirzadeh et al., *Bioconjugate Chem.* 1: 59–65 (1990), is employed. In brief, radiolabeling is performed at pH=4–4.2. The pH of the radiometal solution is adjusted to 3.8–4.0 by addition of several microliters of 3 M NaOAc. The pH of unlabeled HEHA-conjugate is lowered to 4–4.2 by adding the needed amount of 0.15 M $NH_4OAc$ buffer, pH=4.0. To this is added the radiometal and the reaction mixture is left at room temperature for 30 min. The reaction is quenched by raising the pH to ~6 with 3 M NaOAc and any free radiometal is scavenging with 5 ml of 0.5 M $Na_2EDTA$ solution. The product is purified by passage through a TSK-3000 HPLC column (Thompson Instruments) eluted with PBS at 1 ml/min.

Example 7

This example describes the radiolabeling of the HEHA-monoclonal antibody of Example 5 with $^{225}$AC.

$^{225}$Ac $(NO_3)_3$ (2.2–4.0 mCi) was obtained from Oak Ridge National Laboratories (ORNL) as a solid. The solid was taken up in 0.1 M HCl (1 ml), such that the specific activity became 0.22–0.40 mCi/0.1 ml. For radiolabeling the conjugates, an aliquot of $^{225}$Ac solution (0.05–0.2 mCi) was added to the vials containing 0.15 M $NH_4OAc$ (0.3–0.4 ml) at pH 4.0, 5.0 or 7.0. The HEHA-mAb conjugate (0.3–0.4 mg) in 0.15 M $NH_4OAc$ buffer, pH 7.0, was then added. The reaction mixture was incubated for 0.5 hr at 37° C.

Preliminary labeling yields were assessed using 10 cm ITLC-SG strips (Gelman Sciences) spotted with 1 μl of the reaction and developed in 0.15 M $NH_4OAc$ buffer, pH 4.0. In this system the labeled proteins are retained at the origin while $^{225}$Ac acetate moves with the solvent front. The strips were dried, cut into 1-cm segments, and counted in the γ-counter. They were recounted 3 hr later in order to obtain corrected labeling yields for $^{225}$Ac after all of the $^{213}$Bi that had been previously generated decayed.

The reaction was quenched with 0.1 M EDTA, pH 6.0 (4 μl) and $^{225}$Ac-HEHA-mAb conjugate was purified on size exclusion HPLC column as described above. The protein fraction was collected and counted in a Capintec Radioisotope Calibrator and recounted 3 hr later to calculate the specific activity of the product.

The results of radiolabeling of HEHA-mAb conjugates are given in Table I. During preliminary experiments an incubation time of 30 min at 37° C. was found to produce the highest labeling yields while minimizing radiation damage to the antibody. The labeling yields for $^{225}$AC were found to be dependent upon the pH of the reaction mixture with optimal results being obtained at pH 7.0. Labeling yields for $^{213}$Bi, the $^{225}$Ac daughter also present in the reaction mixture in equilibrium with $^{225}$Ac, showed much less dependence on pH below 7.0. Preliminary experiments demonstrated that HEHA-mAb conjugates with an L/P<1.0 resulted in decreased yields, generally lower than 30%. The data in Table I also show that, by maintaining an L/P≧1.0, HEHA-mAb conjugates can be labeled with $^{225}$Ac in 60–85% yield with specific activity of 200–400 μCi/mg protein, which should be easily sufficient to conduct therapy studies in animals.

TABLE I

Dependence of HEHA-mAb labeling yields with $^{225}$Ac and $^{213}$Bi on conjugate concentration, pH of reaction mixture, and initial activity of $^{225}$Ac

| HEHA-mAb conjugate | Amount of conjugate, μg | pH | $^{225}$AC activity, μCi | $^{213}$Bi labeling, % yield | $^{225}$Ac labeling, % yield |
|---|---|---|---|---|---|
| HEHA-BL-3 L/P = 2.0 | 300 | 7.0 | 50 | 80 ± 1 | 60 ± 3 |
|  | 300 | 5.0 | 50 | 75 ± 3 | 43 ± 5 |
|  | 300 | 4.0 | 50 | 67 ± 3 | 22 ± 2 |
|  | 400 | 7.0 | 50 | 78 ± 2 | 75 ± 2 |
|  | 400 | 7.0 | 100 | 82 ± 4 | 72 ± 5 |
|  | 400 | 7.0 | 200 | 80 ± 4 | 85 ± 4 |
| HEHA-T101 L/P = 1.5 | 400 | 7.0 | 100 | 86 ± 5 | 90 ± 3 |

Volume of reaction mixture was 0.4–0.6 ml; all yields are mean values of 3 experiments with SD: $^{213}$Bi was present in reaction in equilibrium with its parent $^{225}$Ac.

Example 8

This example describes the serum stability of the $^{225}$Ac-radiolabeled HEHA-monoclonal antibody of Example 7.

Purified $^{225}$Ac-HEHA-mAb conjugate (200 μl) was incubated with fetal bovine serum (2 ml) for 3 days at 37° C. Aliquots were withdrawn at times 0, 0.25, 1, 3, 5, 24, 48 and 72 hr and analyzed by HPLC on size exclusion column as described above. The radioactive fractions containing high and low molecular weight components were collected and counted on a γ-counter immediately after elution and 3 hr thereafter in order to determine if they were due to free $^{225}$Ac or $^{213}$Bi. If a particular fraction contained $^{225}$Ac/$^{213}$Bi in equilibrium, the results obtained after 3 hr counts were very close to the initial value. In the case of mostly $^{225}$Ac being present, the counts increased 2-fold as the $^{213}$Bi daughter grew in and $^{225}$Ac/$^{213}$Bi reached equilibrium. Finally, the counts decreased 16-fold if mostly $^{213}$Bi was present initially as 3 hr are equal to 4 half-lives of $^{213}$Bi. As a control, free $^{225}$Ac was incubated in serum under the same conditions and aliquots checked by HPLC at the above time points.

The results of serum stability studies of $^{225}$Ac-HEHA-BL-3 conjugate in fetal bovine serum at 37° C. were performed in parallel with serum binding of free $^{225}$Ac (Table II and Supporting Information). The radiolabled HEHA-BL-3 construct preserved its integrity in serum for a period of at least 5 hr releasing less than 1% of $^{225}$Ac and 3% of its daughter $^{213}$Bi. Starting at the 1 hr time point, a peak began to grow in on the trailing slope of the $^{225}$Ac-HEHA-BL-3 peak indicating the presence of species with molecular weight of ~75–100 kDa. After 5 hr of incubation in serum, this peak increased to be approximately one-third of the $^{225}$Ac-HEHA-BL-3 peak. By 24 hr, 42% of $^{225}$Ac was present in serum as the $^{225}$Ac-HEHA complex, which has been previously shown to be very stable in vivo (Deal et al., J. Med. Chem. 42: 2998–2992 (1999)). All free $^{225}$Ac bound instantly to serum proteins, with some trace amounts of radioactivity in the low molecular weight portion of the chromatogram attributable to the $^{213}$Bi daughter.

TABLE II

Results of serum stability studies of $^{225}$Ac-HEHA-BL-3 conjugate in fetal bovine serum at 37° C.

| Time point, hours | $^{225}$Ac activity, associated with $^{225}$Ac-HEHA-BL-3 conjugate, % | $^{213}$Bi activity, associated with $^{225}$Ac-HEHA-BL-3 conjugate, % |
|---|---|---|
| 0 | 100 ± 1 | 100 ± 1 |
| 0.4 | 99 ± 3 | 97 ± 2 |
| 1 | 99 ± 2 | 98 ± 4 |
| 3 | 99 ± 3 | 97 ± 3 |
| 5 | 99 ± 2 | 96 ± 3 |
| 24 | 58 ± 5 | 42 ± 4 |
| 48 | 50 ± 4 | 50 ± 4 |

The values are the mean (n=3±S.D.)

Example 9

This example describes the biodistribution of $^{225}$Ac-HEHA.

$^{225}$Ac complexes were diluted in MES buffer, pH=6.2, to final concentrations of 92, 185, 370 or 740 kBq in 200 μl of solution and injected intravenously into mice. Aliquots were taken from each dilution to serve as external standards for activity determination. Complexes were also evaluated 24 hrs after preparation to confirm stability.

Normal female BALB/c mice were injected with 2.5 μCi in 200 μl MES buffer, pH 6.2, in the tail vein. At 1 hr, 4 hr, 24 hr and 120 hr, 3–5 animals were sacrificed, samples of blood, liver, kidney, spleen, heart and bone were collected and weighed, and the $^{225}$Ac content was determined. The percentage injected dose per gram (% ID/g) was calculated. The results are summarized in Table III.

TABLE III

| | TIME | | | |
|---|---|---|---|---|
| SAMPLE | 1 hr | 4 hr | 24 hr | 120 hr |
| Blood | 0.03 ± 0.01 | 0 | 0 | 0 |
| Liver | 0.17 ± 0.038 | 0.23 ± 0.01 | 0.19 ± 0.02 | 0.26 ± 0.02 |
| Kidney | 0.72 ± 0.17 | 0.71 ± 0.05 | 0.43 ± 0.08 | 0.25 ± 0.07 |
| Spleen | 0.047 ± 0.001 | 0.027 ± 0.01 | 0.03 ± 0 | 0.034 ± 0.001 |
| Heart | 0.055 ± 0.017 | 0.032 ± 0.005 | 0.018 ± 0.009 | 0.026 ± 0.016 |
| Bone | 0.056 ± 0.045 | 0.025 ± 0.004 | 0.013 ± 0.003 | 0.023 ± 0.003 |

Based on the above results, it can be seen that $^{225}$Ac-HEHA is very stable, as demonstrated by the low uptake of the radiocomplex in all tissues, including the liver. In addition, $^{225}$Ac-HEHA showed quick whole-body clearance, with essentially all of the activity excreted by 1 hour.

Example 10

This example describes the use of $^{225}$Ac-HEHA-targeting agent, specifically $^{225}$Ac-HEHA-NCS-J591 mAb, to treat cancer in vivo.

$^{225}$Ac-HEHA-NCS was conjugated to the monoclonal antibody J591, which targets PSMA$_{ext2}$, an antigen that is expressed in prostate tumors and neovasculature. The conjugate was administered to tumor-bearing mice. Administration of the conjugate in an amount that delivered less than one atom of $^{225}$Ac per tumor resulted in significant control of tumor growth. Thus, this example demonstrates the in vivo utility of conjugates of the present invention, in the treatment of disease, such as cancer.

Example 11

This examples describes the attachment of HEHA, which is not bifunctional, to a protein via a carboxycarbonic anhydride.

A HEHA-carboxycarbonic anhydride was prepared by dissolving 50 mg HEHA (HCl)$_6$ in H$_2$O (1 ml) in an acid-washed 5 ml pear-shaped flask and adding triethylamine (140 μl, 17 eq). The solution was lyophilized overnight, and acetonitrile (750 μl) (freshly distilled from CaH$_2$) was added to the white residue. The suspension was sonicated about 10 min to ensure the free base of HEHA was dissolved. The suspension was chilled in an ice bath at 4° C., isobutylchloroformate (8 μl, 1 eq) was added, and the suspension was incubated for 30 min at 4° C. in the refrigerator. The suspension was transferred to an Eppendorf tube and centrifuged for 5 min at 1500 rpm to settle the triethylamine HCl. An aliquot was added to a prepared protein solution (see, e.g., Krejcarek et al., Biochem. Biophys. Res. Commun. 77: 581–585 (1977), for covalent attachment of a chelating group to a macromolecule).

A protein solution was prepared by dissolving 7.2 mg bovine albumin in 1 ml of phosphate-buffered saline solution (PBS) and switched to 50 mM bicarbonate/100 mM NaCl with 5 mM EDTA metal-free conjugation buffer by dialysis at 4° C. The protein was transferred to a reaction vial (flat-bottomed plastic tube with flea bar), the HEHA-carbonic anhydride was added, and the reaction was stirred at 4° C. for 2 hr.

The conjugate was initially purified by dialysis into 0.15 M ammonium acetate at 4° C., followed by continued purification with Centricon-30 spin columns (5–6 washes). The concentration of protein conjugate was estimated from the absorbance at 280 nm (extinction coefficient of 1.4 (ml/(cm×mg)).

All of the references cited herein are hereby incorporated in their entireties by reference.

While this invention has been described with an emphasis upon preferred embodiments, it will be obvious to those of ordinary skill in the art that variations of the preferred compounds and methods may be used and that it is intended that the invention may be practiced otherwise than as specifically described herein. Accordingly, this invention includes all modifications encompassed within the spirit and scope of the invention as defined by the following claims.

What is claimed is:

1. A bifunctional compound of the following formula:

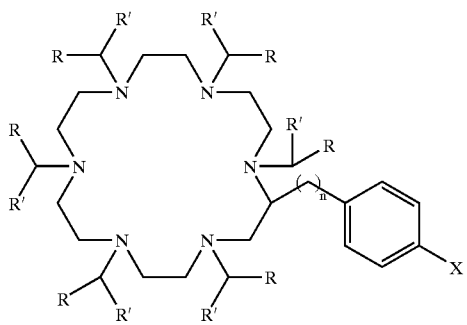

wherein R is $CO_2H$ or CONHR',
R' is selected from the group consisting of H, a $C_1$–$C_8$ alkyl, phenyl and benzyl, wherein said phenyl or benzyl is substituted or unsubstituted,
n is 1–6, and
X is selected from the group consisting of $NO_2$, $NH_2$, NCS, $NHC(O)CH_2Z$, in which Z is selected from the group consisting of Cl, Br and I, and

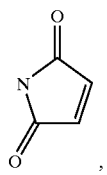

wherein said compound is chelated to $^{225}$Ac.

2. The bifunctional compound of claim 1, wherein R is $CO_2H$ and R' is H or $CH_3$.

3. The bifunctional compound of claim 1, wherein, when R' is phenyl or benzyl, said phenyl or benzyl can be substituted with one or more substituents selected from the group consisting of a $C_1$–$C_6$ alkyl, a halogen, a $C_1$–$C_6$ alkoxy, a $C_1$–$C_6$ hydroxyl, and a $C_1$–$C_6$ polyhydroxyl.

4. A compound comprising the bifunctional compound of claim 1 conjugated to a targeting agent.

5. A compound comprising the bifunctional compound of claim 2 conjugated to a targeting agent.

6. A compound comprising the bifunctional compound of claim 3 conjugated to a targeting agent.

7. A method of treating cancer, which method comprises administering to a patient having cancer a cancer-treatment effective amount of the compound of claim 4 in which the targeting agent is specific for said cancer.

8. A method of treating a solid tumor, which method comprises intratumorally administering to a patient having a tumor a tumor-treatment effective amount of $^{225}$Ac-HEHA or a compound of claim 1 and optionally, simultaneously or sequentially, peritumorally administering to the patient HEHA in an amount effective to chelate any radioactive decay products from $^{225}$Ac-HEHA or the compound.

9. A method of treating cancer, which method comprises administering to a patient having cancer a cancer-treatment effective amount of the compound of claim 5 which the targeting agent is specific for said cancer.

10. A method of treating cancer, which method comprises administering to a patient having cancer a cancer-treatment effective amount of the compound of claim 6 which the targeting agent is specific for said cancer.

11. A method of treating a solid tumor, which method comprises intratumorally administering to a patient having a tumor a tumor-treatment effective amount of a compound of claim 2 and optionally, simultaneously or sequentially, peritumorally administering to the patient HEHA in an amount effective to chelate any radioactive decay products from the compound.

12. A method of treating a solid tumor, which method comprises intratumorally administering to a patient having a tumor a tumor-treatment effective amount of a compound of claim 4 in which the targeting agent is specific for the tumor and optionally, simultaneously or sequentially, peritumorally administering to the patient HEHA in an amount effective to chelate any radioactive decay products from the compound.

13. A method of treating a solid tumor, which method comprises intratumorally administering to a patient having a tumor a tumor-treatment effective amount of a compound of claim 5 in which the targeting agent is specific for the tumor and optionally, simultaneously or sequentially, peritumorally administering to the patient HEHA in an amount effective to chelate any radioactive decay products from the compound.

14. A method of treating a solid tumor, which method comprises intratumorally administering to a patient having a tumor a tumor-treatment effective amount of a compound of claim 6 in which the targeting agent is specific for the tumor and optionally, simultaneously or sequentially, peritumorally administering to the patient HEHA in an amount effective to chelate any radioactive decay products from the compound.

* * * * *